US011175275B2

(12) United States Patent
Fukunaga

(10) Patent No.: US 11,175,275 B2
(45) Date of Patent: Nov. 16, 2021

(54) REPLACEMENT RECOMMENDING DEVICE, REPLACEMENT RECOMMENDING METHOD, AND NON-TRANSITORY STORAGE MEDIUM STORING REPLACEMENT RECOMMENDING PROGRAM

(71) Applicant: TOYOTA JIDOSHA KABUSHIKI KAISHA, Toyota (JP)

(72) Inventor: Takashi Fukunaga, Miyoshi (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 224 days.

(21) Appl. No.: 16/702,651

(22) Filed: Dec. 4, 2019

(65) Prior Publication Data

US 2020/0182853 A1    Jun. 11, 2020

(30) Foreign Application Priority Data

Dec. 11, 2018  (JP) .............................. JP2018-231547

(51) Int. Cl.
 *G01N 33/28*   (2006.01)
 *F01M 11/10*   (2006.01)
 *F01M 1/18*    (2006.01)

(52) U.S. Cl.
 CPC ........... *G01N 33/2888* (2013.01); *F01M 1/18* (2013.01); *F01M 11/10* (2013.01); *F01M 2011/1473* (2013.01)

(58) Field of Classification Search
 CPC ...... G01N 33/2888; F01M 11/10; F01M 1/18; F01M 2011/1473; F01M 2011/14; F02F 11/00; F02F 11/002
 See application file for complete search history.

(56) References Cited

U.S. PATENT DOCUMENTS 4,970,492 A    11/1990 King

FOREIGN PATENT DOCUMENTS

| JP | 2002-317615 A | 10/2002 |
|---|---|---|
| JP | 2010-65637 A | 3/2010 |
| JP | 2014-84786 A | 5/2014 |

*Primary Examiner* — Jacob M Amick
*Assistant Examiner* — Charles J Brauch
(74) *Attorney, Agent, or Firm* — Oblon, McClelland, Maier & Neustadt, L.L.P.

(57) ABSTRACT

A replacement recommending device for a lubricant in an internal combustion engine in which a liquid gasket is applied to a sealing spot includes a processing circuit configured to perform an acquisition process of acquiring temperature information regarding the lubricant in the internal combustion engine, and an output process of outputting a signal indicating that replacement of the lubricant is recommended by operating an output device when a parameter is equal to or greater than a predetermined value based on the temperature information acquired in the acquisition process, the parameter having a value that increases with an increase in a cumulative time in which a temperature of the lubricant is equal to or higher than a prescribed temperature, and the cumulative time being a cumulative time based on a time point at which the liquid gasket is applied to the sealing spot.

9 Claims, 4 Drawing Sheets

REPLACEMENT RECOMMENDING DEVICE, REPLACEMENT RECOMMENDING METHOD, AND NON-TRANSITORY STORAGE MEDIUM STORING REPLACEMENT RECOMMENDING PROGRAM

INCORPORATION BY REFERENCE

The disclosure of Japanese Patent Application No. 2018-231547 filed on Dec. 11, 2018 including the specification, drawings and abstract is incorporated herein by reference in its entirety.

BACKGROUND

1. Technical Field

The disclosure relates to a replacement recommending device, a replacement recommending method, and a non-transitory storage medium storing a replacement recommending program for a lubricant in an internal combustion engine in which a liquid gasket is applied to a sealing spot.

2. Description of Related Art

For example, an internal combustion engine in which a liquid gasket is applied to a sealing spot is described in Japanese Patent Application Publication No. 2014-84786 (JP 2014-84786 A).

SUMMARY

Since a part of a liquid gasket is exposed in the vicinity of a sealing spot, or the like, the liquid gasket comes into contact with a lubricant in the internal combustion engine. When the temperature of the lubricant is high, silicone contained in the liquid gasket is likely to be eluted into the lubricant. When a silicone concentration in the lubricant is high, there is a possibility that a bubble fraction may increase. The bubble fraction is a ratio of a volume of bubbles to a volume of the lubricant.

1. A first aspect of the disclosure relates to a replacement recommending device for a lubricant in an internal combustion engine in which a liquid gasket is applied to a sealing spot. The replacement recommending device includes a processing circuit configured to perform an acquisition process of acquiring temperature information regarding the lubricant in the internal combustion engine, and an output process of outputting a signal indicating that replacement of the lubricant is recommended by operating an output device when a parameter is equal to or greater than a predetermined value based on the temperature information acquired in the acquisition process, the parameter having a value that increases with an increase in a cumulative time in which a temperature of the lubricant is equal to or higher than a prescribed temperature, and the cumulative time being a cumulative time based on a time point at which the liquid gasket is applied to the sealing spot.

Since an amount of silicone eluted from the liquid gasket into the lubricant increases as the cumulative time increases, it is considered that a bubble fraction in the lubricant increases when the value of the parameter increases. Therefore, with the above-mentioned configuration, by outputting the signal indicating that the replacement of the lubricant is recommended when the value of the parameter is equal to or greater than the predetermined value, it is possible to recommend the replacement of the lubricant when the bubble fraction increases and to prompt a user to improve a situation in which the lubricant having a high bubble fraction is used.

2. The output process may include a calculation process of dividing a temperature area that is equal to or higher than a predetermined temperature into a plurality of temperature subareas and calculating, as the parameter, a sum of values each of which is obtained by multiplying a cumulative time in which the temperature of the lubricant acquired in the acquisition process is in a corresponding one of the temperature subareas, by a weighting factor, and a determination process of determining whether the sum is equal to or greater than the predetermined value, the weighting factors for the temperature subareas being set such that a weighting factor for a higher temperature subarea among the weighting factors is greater than a weighting factor for a lower temperature subarea among the weighting factors, temperatures of the higher temperature subarea being higher than temperatures of the lower temperature subarea. The output process may be a process of outputting the signal indicating that the replacement of the lubricant is recommended when the sum is determined to be equal to or greater than the predetermined value. The predetermined temperature may be lower than the prescribed temperature.

In this configuration, the sum, which is the parameter referred to for outputting the signal indicating that the replacement of the lubricant is recommended, is calculated based on the time in which the temperature of the lubricant is in each of the temperature subareas. This sum has a value which increases as a proportion of the time in which the temperature of the lubricant is in a higher temperature subarea increases even when the cumulative time in which the temperature of the lubricant is equal to or higher than the predetermined temperature remains the same. Accordingly, with the above-mentioned configuration, it is possible to determine whether the signal indicating that the replacement of the lubricant is recommended should be output, in consideration of tendencies that silicone of the liquid gasket is more likely to be eluted into the lubricant and the bubble fraction in the lubricant is more likely to increase as the temperature of the lubricant increases.

3. The replacement recommending device may be located outside a vehicle in which the internal combustion engine is mounted and includes a storage device and a communication device. The acquisition process may include a process of storing, in the storage device, the temperature information regarding the lubricant acquired by communication using the communication device. The calculation process may be a process of calculating the sum based on time-series data regarding the temperature of the lubricant stored in the storage device. The output process may be a process of outputting the signal indicating that the replacement of the lubricant is recommended to a dealer of the vehicle by operating the communication device serving as the output device.

With this configuration, a dealer can determine that the replacement of the lubricant is recommended, and the dealer can announce to a user that the replacement of the lubricant is recommended.

4. The acquisition process may include a process of acquiring information indicating that the lubricant has been replaced. The processing circuit may be configured not to perform the output process when there is information indicating that the lubricant has been replaced after the time point at which the liquid gasket is applied to the sealing spot.

The phenomenon in which silicone contained in the liquid gasket is eluted into the lubricant becomes marked in a state in which the liquid gasket has just been applied, and an amount of the liquid gasket exposed from the sealing spot decreases with the lapse of time. Therefore, an amount of silicone eluted into the lubricant decreases. Accordingly, in the case where a certain cumulative time in which the internal combustion engine operates has elapsed after the liquid gasket is applied, an increase in the bubble fraction in the lubricant due to elution of silicone can be ignored after the lubricant is replaced. Therefore, with the above-mentioned configuration, when there is information indicating that the lubricant has been replaced, the output process is not performed, and thus, it is possible to prevent an unnecessary announcement to a user.

5. The replacement recommending device may be mounted in a vehicle in which the internal combustion engine is mounted. The output process may be a process of outputting the signal indicating that the replacement of the lubricant is recommended by operating an alarm serving as the output device.

With this configuration, it is possible to recommend the replacement of the lubricant in the vehicle by operating the alarm in the vehicle.

6. A second aspect of the disclosure relates to a replacement recommending method of recommending replacement of a lubricant in an internal combustion engine in which a liquid gasket is applied to a sealing spot. The replacement recommending method includes causing one or more computers to perform an acquisition process of acquiring temperature information regarding the lubricant in the internal combustion engine, and an output process of outputting a signal indicating that the replacement of the lubricant is recommended by operating an output device when a parameter is equal to or greater than a predetermined value based on the temperature information acquired in the acquisition process, the parameter having a value that increases with an increase in a cumulative time in which a temperature of the lubricant is equal to or higher than a prescribed temperature, and the cumulative time being a cumulative time based on a time point at which the liquid gasket is applied to the sealing spot.

The output process may include a calculation process of dividing a temperature area that is equal to or higher than a predetermined temperature into a plurality of temperature subareas and calculating, as the parameter, a sum of values each of which is obtained by multiplying a cumulative time in which the temperature of the lubricant acquired in the acquisition process is in a corresponding one of the temperature subareas, by a weighting factor, and a determination process of determining whether the sum is equal to or greater than the predetermined value, the weighting factors for the temperature subareas being set such that a weighting factor for a higher temperature subarea among the weighting factors is greater than a weighting factor for a lower temperature subarea among the weighting factors, temperatures of the higher temperature subarea being higher than temperatures of the lower temperature subarea. The output process may be a process of outputting the signal indicating that the replacement of the lubricant is recommended when the sum is determined to be equal to or greater than the predetermined value. The predetermined temperature may be lower than the prescribed temperature.

With the above-mentioned configuration, it is possible to achieve the same advantageous effects as those of configuration 1 or 2.

7. A third aspect of the disclosure relates to a non-transitory storage medium storing a replacement recommending program that is a program for recommending replacement of a lubricant in an internal combustion engine in which a liquid gasket is applied to a sealing spot, the replacement recommending program being executable by one or more computers, and causing the one or more computers to perform processes. The processes include an acquisition process of acquiring temperature information regarding the lubricant in the internal combustion engine, and an output process of outputting a signal indicating that the replacement of the lubricant is recommended by operating an output device when a parameter is equal to or greater than a predetermined value based on the temperature information acquired in the acquisition process, the parameter having a value that increases with an increase in a cumulative time in which a temperature of the lubricant is equal to or higher than a prescribed temperature, and the cumulative time being a cumulative time based on a time point at which the liquid gasket is applied to the sealing spot.

The output process may include a calculation process of dividing a temperature area that is equal to or higher than a predetermined temperature into a plurality of temperature subareas and calculating, as the parameter, a sum of values each of which is obtained by multiplying a cumulative time in which the temperature of the lubricant acquired in the acquisition process is in a corresponding one of the temperature subareas, by a weighting factor, and a determination process of determining whether the sum is equal to or greater than the predetermined value, the weighting factors for the temperature subareas being set such that a weighting factor for a higher temperature subarea among the weighting factors is greater than a weighting factor for a lower temperature subarea among the weighting factors, temperatures of the higher temperature subarea being higher than temperatures of the lower temperature subarea. The output process may be a process of outputting the signal indicating that the replacement of the lubricant is recommended when the sum is determined to be equal to or greater than the predetermined value. The predetermined temperature may be lower than the prescribed temperature.

With the above-mentioned configuration, it is possible to achieve the same advantageous effects as those of configuration 1 or 2.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein.

DETAILED DESCRIPTION OF EMBODIMENTS

Figure 1:
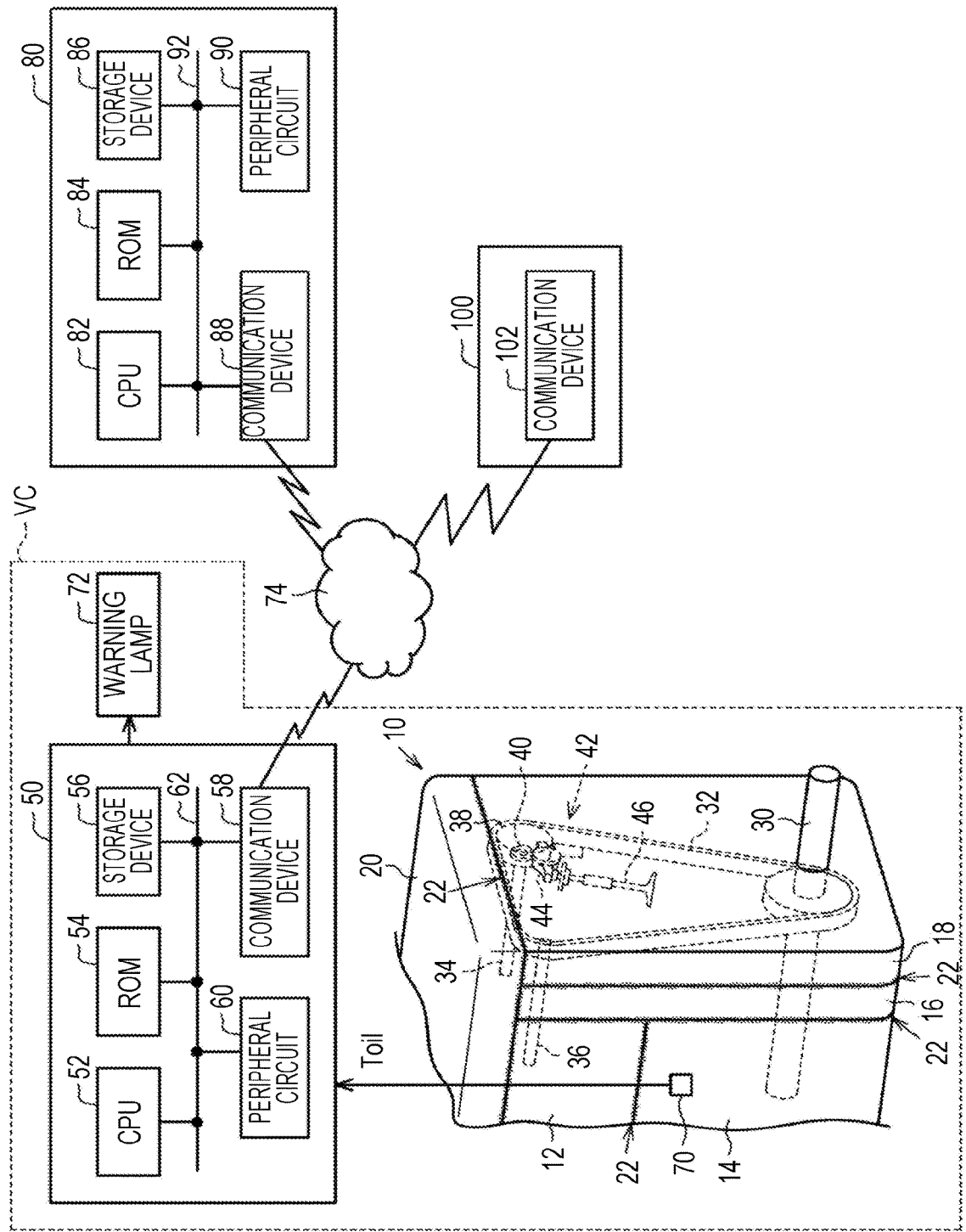
FIG. 1 is a diagram illustrating a part of a vehicle, a center, and a dealer according to a first embodiment.

Hereinafter, a replacement recommending device according to a first embodiment will be described with reference to the accompanying drawings. An internal combustion engine 10 illustrated in FIG. 1 is mounted in a vehicle VC. In the internal combustion engine 10, a first chain cover 16 and a second chain cover 18 are fastened to a cylinder head 12 and a cylinder block 14 with bolts in a state in which the first chain cover 16 is interposed between the cylinder head 12 and the cylinder block 14, and the second chain cover 18. A head cover 20 is fastened to the cylinder head 12, the first chain cover 16, and the second chain cover 18 with bolts. A liquid gasket 22 (FIPG: Formed In Place Gasket) is provided between the cylinder head 12 and the cylinder block 14, between the head cover 20 and each of the cylinder head 12, the first chain cover 16, and the second chain cover 18, between the first chain cover 16 and the second chain cover 18, and the like.

Rotary power of a crank shaft 30 is transmitted to an intake-side cam shaft 34 and an exhaust-side cam shaft 36 via a chain 32. Specifically, in this embodiment, the power of the crank shaft 30 is transmitted to the intake-side cam shaft 34 via a hydraulic intake-side valve timing varying device 38.

An intake-side cam 40 is attached to the intake-side cam shaft 34. One end of a rocker arm 44 is supported by a lash adjuster 42, and the rocker arm 44 is pressed by the intake-side cam 40 due to rotation of the intake-side cam shaft 34, and thus an intake valve 46 is opened.

A control device 50 controls the internal combustion engine 10 and operates an operation unit of the internal combustion engine 10, for example, the intake-side valve timing varying device 38, to control a torque and an exhaust gas component proportion which are controlled variables of the internal combustion engine. The control device 50 refers to a temperature of a lubricant (an oil temperature Toil) which is detected by an oil temperature sensor 70 at the time of control of the controlled variables.

The control device 50 includes a CPU 52, a ROM 54, a storage device 56, a communication device 58, and a peripheral circuit 60, which are connected to each other via a communication line 62. The peripheral circuit 60 includes a circuit that generates a clock signal for regulating internal operations, a power supply circuit, and a reset circuit. The CPU 52 is started when control of the internal combustion engine 10 is requested by the peripheral circuit 60 and is stopped when control of the internal combustion engine 10 is not requested.

A center 80 receives and collects data, which is transmitted from the communication device 58 of each of a plurality of vehicles VC, via a network 74. The center 80 includes a CPU 82, a ROM 84, a storage device 86, a communication device 88, and a peripheral circuit 90, which are connected to each other via a communication line 92.

A dealer 100 sells vehicles VC. The dealer 100 includes a communication device 102 and receives data which is transmitted by the communication device 88 of the center 80 via the network 74.

After a vehicle ID of a vehicle VC is registered at the center, the control device 50 transmits various data which is generated in the vehicle VC to the center 80 along with a time stamp indicating a time at which the data is generated and the vehicle ID which is identification information on the vehicle VC. The center 80 collects and analyzes data which is transmitted from a plurality of vehicles VC. Particularly, the center 80 outputs a signal indicating that replacement of a lubricant is recommended to the dealer 100 based on a history of an oil temperature Toil. Since the CPU 52 of the control device 50 is started when control of the internal combustion engine 10 is requested, a period in which the CPU 52 samples the oil temperature Toil includes a period in which the internal combustion engine 10 operates and does not include a period in which the internal combustion engine 10 stops even when the stopping period overlaps a part of the sampling period.

Figure 2:
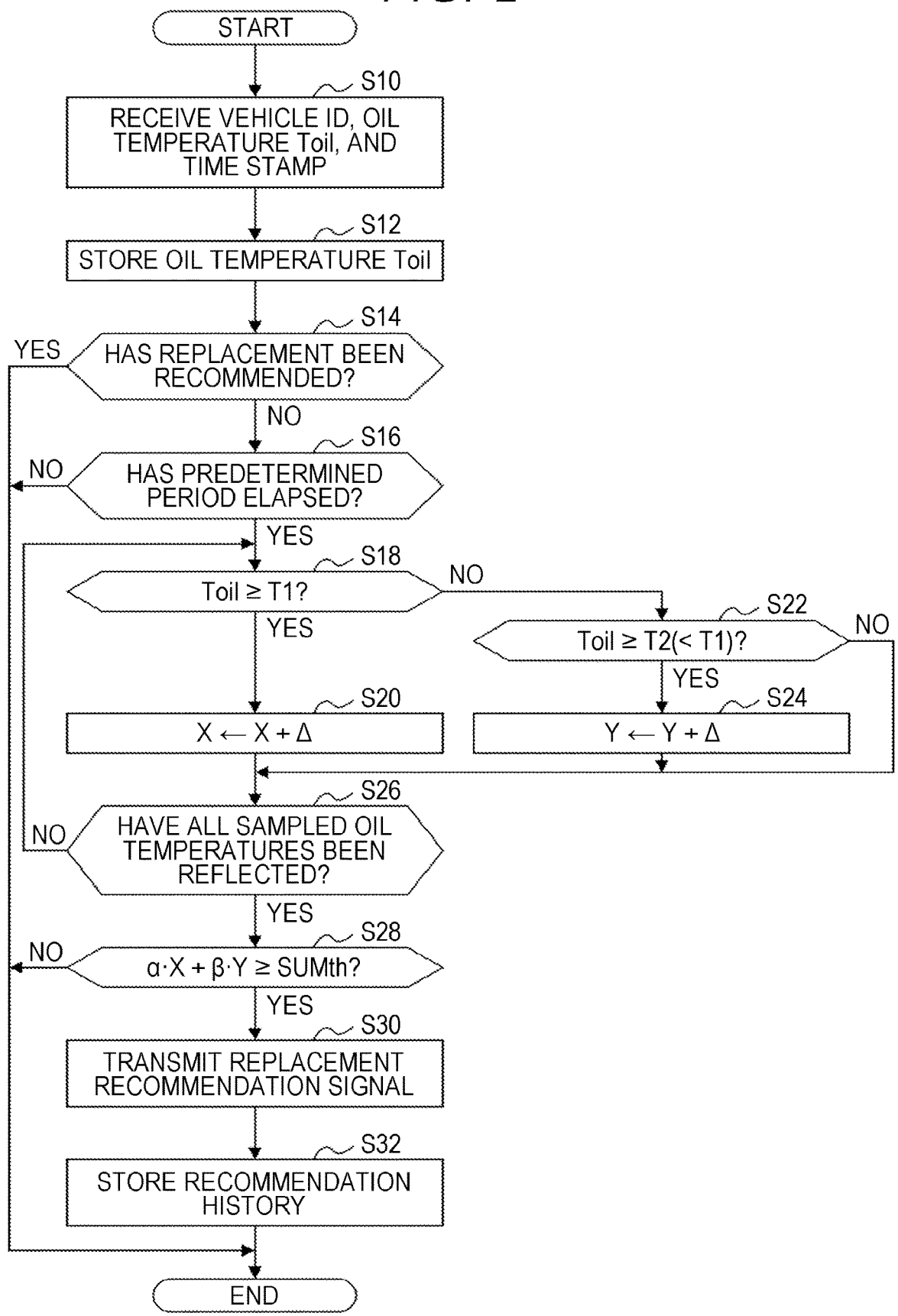
FIG. 2 is a flowchart illustrating a process routine which is performed by the center according to the first embodiment.

FIG. 2 illustrates a process routine which is performed by the center 80. The process routine illustrated in FIG. 2 is embodied by causing the CPU 82 to repeatedly execute a program stored in the ROM 84, for example, at intervals of a predetermined period. In the following description, step numbers of processes are denoted by numerals prepended with S.

In the series of processes illustrated in FIG. 2, the CPU 82 first receives a time stamp for identifying a time at which an oil temperature Toil is detected, the oil temperature Toil, and a vehicle ID which are data transmitted from a vehicle VC (S10). Then, the CPU 82 stores the oil temperature Toil along with the corresponding time stamp in an area allocated to the vehicle ID in a storage area of the storage device 86 (S12). Then, the CPU 82 determines whether replacement of a lubricant in the internal combustion engine 10 has already been recommended for a vehicle VC which is identified by the vehicle ID (S14). Then, when it is determined that replacement of a lubricant has not been recommended (S14: NO), the CPU 82 determines whether a predetermined period has elapsed (S16). Here, the predetermined period can be set to, for example, a period in which a predetermined number of sampled values of the oil temperature Toil which have not been processed in S18 to S24 (described later) are stored. In this case, when a predetermined number of sampled values of the oil temperature Toil which have not been processed in S18 to S24 are stored, the CPU 82 determines that the predetermined period has elapsed. The predetermined period is not limited thereto and may be set to, for example, a time point at which a predetermined time such as one month has elapsed.

When the CPU 82 determines that the predetermined period has elapsed (S16: YES), the CPU 82 reads one of the oil temperatures Toil received in the predetermined period from the storage device 86, and determines whether the read oil temperature Toil is equal to or higher than a prescribed temperature T1 (S18). The prescribed temperature T1 is set to a temperature at which silicone contained in the liquid gasket 22 located in a spot in contact with a lubricant, such as the liquid gasket 22 which protrudes from between the first chain cover and each of the cylinder head 12 and the cylinder block 14, is eluted into the lubricant. When the CPU 82 determines that the oil temperature Toil is equal to or higher than the prescribed temperature T1 (S18: YES), the CPU 82 increases a cumulative time X in which the oil temperature Toil is equal to or higher than the prescribed temperature T1, by a predetermined value Δ (S20). Here, the predetermined value Δ is set to a sampling interval of the oil temperature Toil.

On the other hand, when the CPU 82 determines that the oil temperature Toil is lower than the prescribed temperature T1 (S18: NO), the CPU 82 determines whether the oil temperature Toil is equal to or higher than a predetermined temperature T2 (S22). The predetermined temperature T2 is set to a temperature which is lower than the prescribed temperature T1 and at which silicone contained in the liquid gasket 22 located in a spot in contact with the lubricant is eluted into the lubricant (for example, a temperature equal to or higher than 90° C.). When the CPU 82 determines that the oil temperature Toil is equal to or higher than the predetermined temperature T2 (S22: YES), the CPU 82 increases a cumulative time Y in which the oil temperature Toil is equal to or higher than the predetermined temperature T2 and less than the prescribed temperature T1, by a predetermined value Δ (S24).

When the processes of S20 and S24 have been completed or when the determination result of S22 is negative, the CPU 82 determines whether the processes of S18 to S24 have been performed on all the oil temperatures Toil received in the predetermined period (S26). Then, when the CPU 82 determines that the processes have not been performed on all the oil temperatures (S26: NO), the CPU 82 returns to the process of S18 and performs the processes of S18 to S24 on an oil temperature Toil which has not been processed in S18 to S24 out of the oil temperatures Toil received in the predetermined period.

On the other hand, when the CPU 82 determines that all the oil temperatures Toil received in the predetermined period have been processed in S18 to S24 (S26: YES), the CPU 82 determines whether a sum of a value obtained by multiplying the cumulative time X by a weighting factor α and a value obtained by multiplying the cumulative time Y by a weighting factor β is equal to or greater than a predetermined value SUMth (S28). The sum is a parameter indicating an amount of silicone eluted from the liquid gasket into the lubricant. Since silicone which is contained in the liquid gasket 22 is more likely to be eluted into the lubricant when the oil temperature Toil is high than when the oil temperature Toil is low, the weighting factor α is set to a value greater than the weighting factor β. The predetermined value SUMth is set to a value indicating that an amount of silicone contained in the lubricant is such a large amount that replacement of the lubricant is recommended.

When the CPU 82 determines that the sum is equal to or greater than the predetermined value SUMth (S28: YES), the CPU 82 transmits a signal indicating that replacement of the lubricant is recommended and including the vehicle ID to the dealer 100 which has sold the vehicle identified by the vehicle ID, by operating the communication device 88 (S30). Then, the CPU 82 stores the vehicle ID of the vehicle VC and history information indicating that replacement of the lubricant has been recommended in the storage device 86 in association with each other (S32).

When the process of S32 has been completed or when the determination results of S14, S16, and S28 are negative, the CPU 82 ends the series of processes illustrated in FIG. 2. Operations and advantages in this embodiment will be described below.

On the vehicle VC side, the CPU 52 samples an oil temperature Toil sequentially when the internal combustion engine 10 operates, adds a time stamp for specifying the time at which the oil temperature Toil is sampled, and stores the result in the storage device 56. Then, when the number of sampled oil temperatures Toil increases to a certain extent, the CPU 52 transmits the oil temperatures Toil stored in the storage device 56 to the center 80 along with the corresponding time stamps and the corresponding vehicle ID. The CPU 82 of the center 80 calculates the cumulative time X in which the oil temperature Toil is equal to or higher than the prescribed temperature T1 and the cumulative time Y in which the oil temperature Toil is equal to or higher than the predetermined temperature T2 and less than the prescribed temperature T1 for each vehicle VC which is identified by the vehicle ID. Here, since the oil temperature Toil is transmitted from the vehicle VC to the center 80 along with the vehicle ID after the vehicle ID of the vehicle VC is registered at the center 80, each of the cumulative times X and Y for each vehicle VC identified by the vehicle ID can be considered to be a cumulative time based on the time point at which the liquid gasket 22 is applied (i.e., a cumulative time from the time point at which the liquid gasket 22 is applied). That is, the time point at which the vehicle ID is registered at the center 80 is regarded as a time point at which a liquid gasket is applied to a sealing spot.

The CPU 82 of the center 80 updates the cumulative time X in which the oil temperature Toil is equal to or higher than the prescribed temperature T1 and the cumulative time Y in which the oil temperature Toil is equal to or higher than the predetermined temperature T2 and less than the prescribed temperature T1 using the sampled values of the oil temperature Toil transmitted within a predetermined period each time the predetermined period elapses. That is, each time time-series data regarding the oil temperature Toil, which is most recently sampled with the lapse of time, is stored in the storage device 86 of the center 80, the cumulative times X and Y are updated based on the newly sampled oil temperature Toil. The cumulative times X and Y do not change or increase when they are updated. That is, when all the newly sampled oil temperatures Toil are less than the predetermined temperature T2, the cumulative times X and Y do not change.

Then, the CPU 82 determines whether replacement of the lubricant is recommended based on the cumulative times X and Y When the CPU 82 determines that replacement of the lubricant is recommended, the CPU 82 transmits a signal indicating the determination result and the vehicle ID to the dealer 100. Accordingly, the dealer 100 determines whether there is a history that the lubricant has been replaced at the dealer 100 after a user of the vehicle VC identified by the vehicle ID has purchased the vehicle VC, and announces that replacement of the lubricant is recommended when there is no history, because a lubricant in a new vehicle may deteriorate exceptionally early.

Accordingly, it is possible to prompt a user to eliminate the situation in which a bubble fraction (a bubble rate) in the lubricant may be excessively increased due to elution of a large amount of silicone into the lubricant. Here, the bubble fraction is a ratio of a volume of bubbles contained in the lubricant to a volume of the lubricant.

When the bubble fraction is great, there is a possibility that inconveniences may occur. For example, an insufficient oil pressure may be applied to a valve system such as the lash adjuster 42 or the intake-side valve timing varying device 38. Accordingly, by announcing that replacement of the lubricant is recommended, it is possible to enhance the likelihood that the lubricant will be replaced before the possibility of occurrence of inconveniences increases. In addition, in comparison with a case in which a user is informed of a timing at which a lubricant should be replaced when the user purchases a new vehicle, it is possible to prevent a user from visiting the dealer 100 at a time point at which the lubricant does not actually need to be replaced. That is, the cumulative time in which the oil temperature Toil is high may decrease depending on how a user drives a vehicle, and the determination result of S28 may be negative even at an ordinary replacement timing for a lubricant. When a user purchases a new vehicle, the user may be informed of an early replacement timing because an amount of silicone eluted from the liquid gasket 22 into the lubricant increases before the lubricant is replaced for the first time after the new vehicle is purchased. In such a case, the user may unnecessarily visit the dealer at a timing at which the lubricant does not need to be replaced. On the other hand, according to this embodiment, only when the cumulative time in which the oil temperature Toil is high is increased due to the manner in which a user drivers the vehicle VC and replacement of the lubricant is recommended earlier than a normal replacement timing for the lubricant, the user is notified of the recommendation.

A second embodiment will be described below with reference to the drawings with a focus on differences from the first embodiment.

In the above-mentioned embodiment, even when a lubricant has been already replaced, the information indicating that the lubricant has been already replaced is not provided to the center 80. On the other hand, in this embodiment, when a lubricant has been replaced, the information indicating that the lubricant has been already replaced is transmitted to the center 80. This can be embodied, for example, when the dealer 100 inputs, to the control device 50, a signal for prompting the control device 50 to transmit information indicating that the lubricant has been replaced to the center 80 in the case where the lubricant is replaced in the dealer 100.

Figure 3:
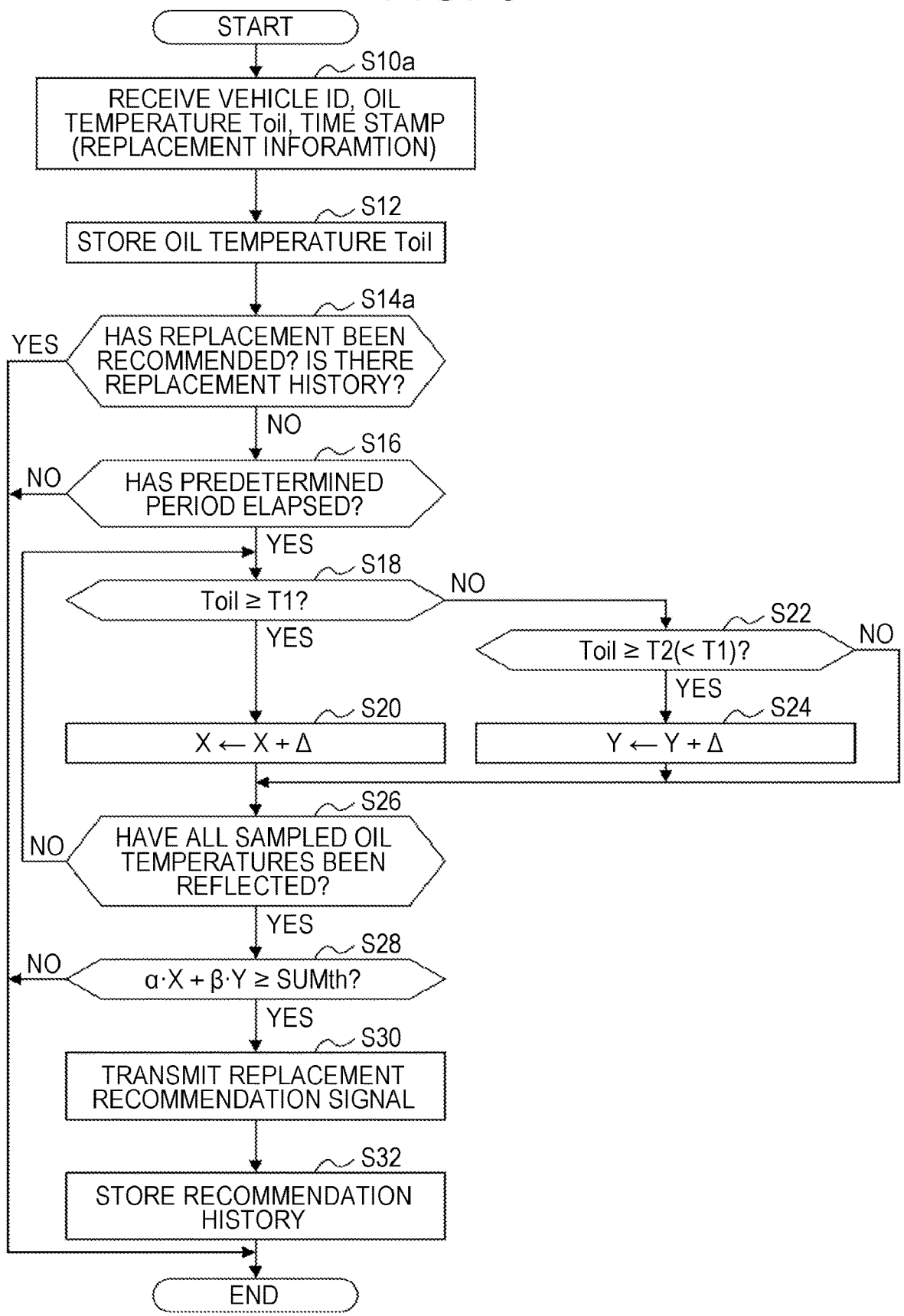
FIG. 3 is a flowchart illustrating a process routine which is performed by a center according to a second embodiment.

FIG. 3 illustrates a process routine which is performed by the center 80. The process routine illustrated in FIG. 3 is embodied by causing the CPU 82 to repeatedly execute a program stored in the ROM 84, for example, at intervals of a predetermined period. The processes in FIG. 3 corresponding to the processes illustrated in FIG. 2 will be denoted by the same step numbers and description thereof will not be repeated.

In a series of processes illustrated in FIG. 3, the CPU 82 first receives a vehicle ID, an oil temperature Toil, a time stamp for identifying a time at which the oil temperature Toil is detected, and information (replacement information) indicating that the lubricant has been replaced when there is the replacement information (S10a), and then performs the process of S12. When the process of S12 is completed, the CPU 82 determines whether a logical sum (logical OR) of the conditions is true. The logical sum (logical OR) is a logical sum of the condition that there is a history indicating that replacement of the lubricant has been recommended by performing the process of S30 and the condition that history information indicating that the lubricant has been replaced is received through the process of S10a (S14a). That is, the CPU 82 determines whether at least one of the conditions is satisfied. Then, the CPU 82 performs the process of S16 when the CPU 82 determines that the logical sum is not true (S14a: NO), and ends the series of processes illustrated in FIG. 3 when the CPU 82 determines that the logical sum is true (S14a: YES).

In this way, in this embodiment, when the lubricant has been already replaced, the center 80 does not output a signal indicating that replacement of the lubricant is recommended to the dealer 100 and thus it is possible to reduce labor of the dealer 100 for determining whether there is a history that the lubricant has been replacement.

A third embodiment will be described below with reference to the drawings with a focus on differences from the first embodiment.

In the above-mentioned embodiment, whether replacement of a lubricant is recommended is determined by the center 80, but is determined by the control device 50 in this embodiment. In this embodiment, when a lubricant is replaced in the dealer 100, history information indicating that the lubricant has been replaced is stored in the storage device 56 of the control device 50 by the dealer 100.

Figure 4:
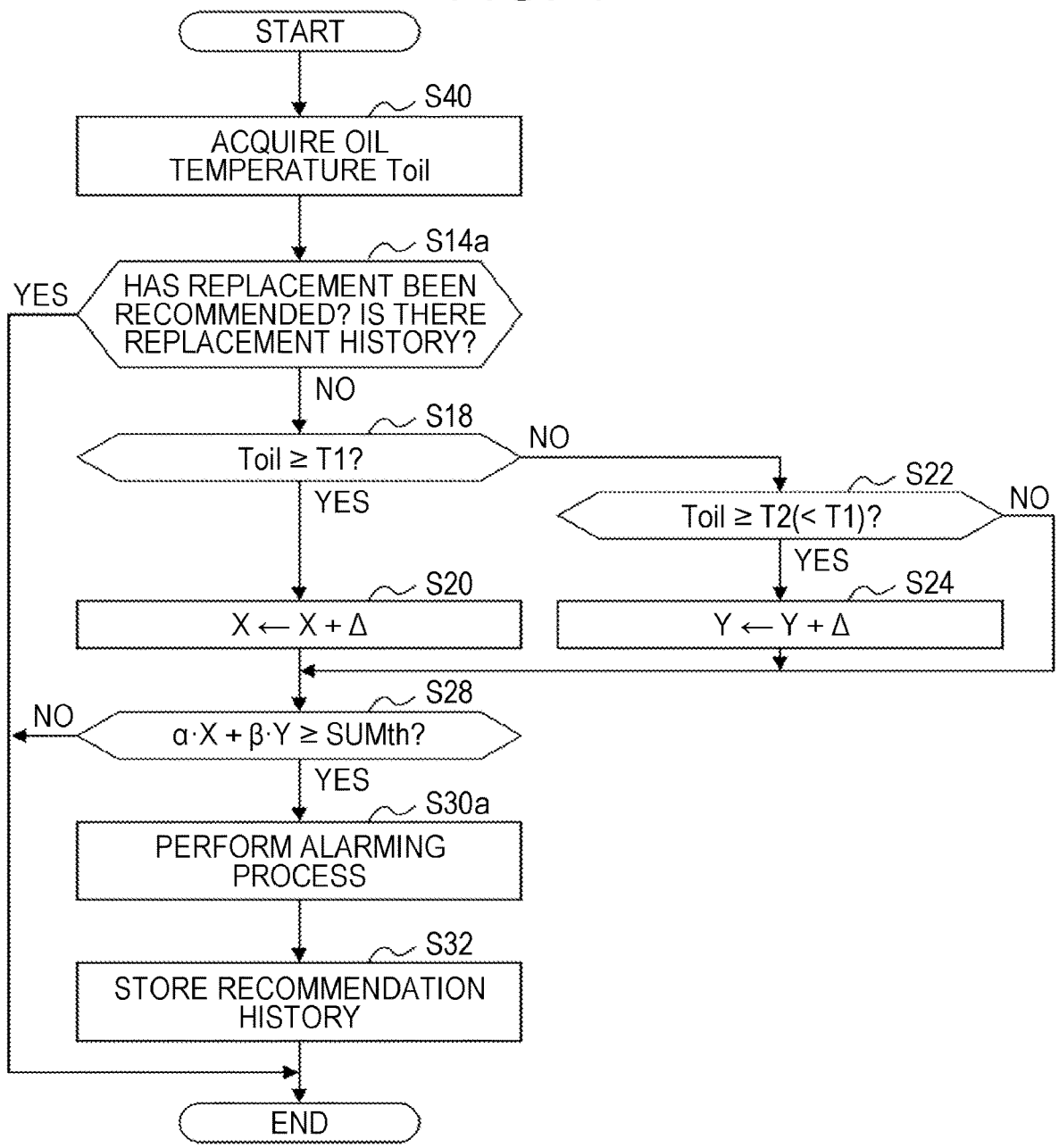
FIG. 4 is a flowchart illustrating a process routine which is performed by a control device according to a third embodiment.

FIG. 4 illustrates a process routine which is performed by the control device 50. The process routine illustrated in FIG. 4 is embodied by causing the CPU 52 to repeatedly execute a program stored in the ROM 54, for example, at intervals of a predetermined period. The processes in FIG. 4 corresponding to the processes illustrated in FIG. 2 will be denoted by the same step numbers and description thereof will not be repeated.

In a series of processes illustrated in FIG. 4, the CPU 52 first acquires an oil temperature Toil (S40). Then, the CPU 52 determines whether a logical sum (logical OR) is true. The logical sum (logical OR) is a logical sum of a condition that there is a history indicating that replacement of the lubricant has been recommended and a condition that history information indicating that the lubricant has been replaced is stored in the storage device 56 (S14a). Then, the CPU 52 performs the process of S18 when the CPU 52 determines that the logical sum is not true (S14a: NO), and ends the series of processes illustrated in FIG. 4 when the CPU 52 determines that the logical sum is true (S14a: YES). When the determination result of S28 is positive, the CPU 52 notifies a user that replacement of the lubricant is recommended by operating a warning lamp 72 illustrated in FIG. 1 (S30a) and then performs the process of S32.

A replacement recommending device corresponds to the center 80 in the first embodiment and the second embodiment and corresponds to the control device 50 in the third embodiment. A processing circuit corresponds to the CPU 82 and the ROM 84 in the first embodiment and the second embodiment and corresponds to the CPU 52 and the ROM 54 in the third embodiment. An acquisition process corresponds to the processes of S10 and S12 in FIG. 2, corresponds to the processes of S10a and S12 in FIG. 3, and corresponds to the process of S40 in FIG. 4. An output process corresponds to the processes of S18 to S30 in FIGS. 2 and 3 and corresponds to the processes of S18 to S28 and S30a in FIG. 4. An output device corresponds to the communication device 88 in the process routine in FIG. 2 or 3 and corresponds to the warning lamp 72 in the process routine in FIG. 4. A computer corresponds to the CPU 82 in the first embodiment and the second embodiment and corresponds to the CPU 52 in the third embodiment. A parameter corresponds to "α·X+β·Y" A calculation process corresponds to the processes of S18 to S28, and a determination process corresponds to the process of S28. A storage device corresponds to the storage device 86. An acquisition process corresponds to the processes of S10a and S12, and "not perform the output process" corresponds to not performing the process of S16 to S28 when the determination result of S14a is positive. An alarm corresponds to the warning lamp 72.

The embodiments can be modified as follows. The embodiments and the following modifications can be embodied in combination with each other as long as they are not technically contradictory to each other.

The cumulative time will be described below. In the above-mentioned embodiments, each of the cumulative time X and the cumulative time Y is set based on the time point at which a liquid gasket is applied, and is not necessarily based on a time in which the internal combustion engine 10 operates. However, the disclosure is not limited to this configuration. The cumulative time may be set based on the time point at which a liquid gasket is applied, and also based on a time in which the internal combustion engine 10 operates.

The calculation process will be described below. In the above-mentioned embodiments, the bubble fraction in a lubricant is quantified by weighting the cumulative time X in which the oil temperature Toil is equal to or higher than the prescribed temperature T1 and the cumulative time Y in which the oil temperature Toil is equal to or higher than the predetermined temperature T2 and less than the prescribed temperature T1. However, the disclosure is not limited to this configuration. For example, the bubble fraction may be quantified by dividing a temperature area into three or more temperature subareas and summing values obtained by weighting withe use of weighting factors which correspond to the temperature subareas. A weighting factor for a higher temperature subareas is greater than a weighting factor for a lower temperature subarea. Temperatures of the higher temperature subarea are higher than temperatures of the lower temperature subarea.

The output process will be described below. Use of different weighting factors for a plurality of temperature subareas is not essential, and the bubble fraction may be quantified, for example, using a cumulative time in which the oil temperature is equal to or higher than the predetermined temperature T2. In this case, a signal indicating that replacement of the lubricant is recommended may be output when the cumulative time is equal to or greater than a predetermined time.

The signal indicating that replacement of the lubricant is recommended is output to the dealer 100 in the process routines illustrated in FIGS. 2 and 3, but the disclosure is not limited to this configuration. For example, the signal may be output to a vehicle or a mobile terminal carried by a user of the vehicle.

The information on the time point at which the liquid gasket is applied to a sealing spot will be described below. In the above-mentioned embodiments, the time point at which a vehicle ID or the like is registered in the center 80 is regarded as the time point at which the liquid gasket is applied to a sealing spot, but the disclosure is not limited to this configuration. For example, when a component is replaced due to a failure of the internal combustion engine 10 or the like, the dealer 100 or the control device 50 may transmit the information to the center 80, and the center 80 may initialize the cumulative times X and Y for the vehicle identified by the vehicle ID when receiving the information. Accordingly, since the cumulative times X and Y are based on the time point at which the information is received, the time point at which the liquid gasket is applied to a sealing spot is updated based on the initialization time point.

The alarm will be described below. In the above-mentioned embodiments, the warning lamp 72 is used as the alarm, but the disclosure is not limited to a device that outputs visual information. For example, a device that outputs auditory information may be used.

The replacement recommending device will be described below. The replacement recommending device is not limited to the control device 50 or the center 80. For example, the process routine illustrated in FIG. 2 or 3 may be performed by a mobile terminal carried by a user. This can be embodied by installing an application program for causing a computer to perform the process routine illustrated in FIG. 2 or 3 in the mobile terminal. In this case, the process of S30a may be performed instead of the process of S30. That is, an alarming process of displaying a message indicating that replacement is recommended, for example, on a display of the mobile terminal may be performed.

The processing circuit will be described below. The processing circuit is not limited to a circuit including the CPU 52 and the ROM 54 and performing software processes or a circuit including the CPU 82 and the ROM 84 and performing software processes. For example, a dedicated hardware circuit (for example, an Application Specific Integrated Circuit (ASIC)) that performs at least some of the software processes by hardware may be provided in the above-mentioned embodiments. That is, the processing circuit may have one of configurations (a) to (c) which will be described below. (a) The processing circuit includes a processor performing all the processes in accordance with a program and a program storage device such as a ROM storing the program. (b) The processing circuit includes a processor performing some of the processes in accordance with a program, a program storage device, and a dedicate hardware circuit performing the other processes. (c) The processing circuit includes a dedicated hardware circuit performing all the processes. Here, the number of software processing circuits or dedicated hardware circuits including the processor and the program storage device may be two or more.

The computer will be described below. The computer may be modified similarly to the processing circuit. The storage device and the computer (the processing circuit) may not be disposed in one spot. For example, the storage device 86 may be disposed in the center 80 and the processing circuit performing the processes of S14 (S14a) to S30 may be disposed in the dealer 100. The computers may not be disposed in one spot. That is, for example, a computer performing the processes S10 to S26 in FIG. 2 and a computer performing the process of S28 may be disposed in different spots.

What is claimed is:

1. A replacement recommending device for a lubricant in an internal combustion engine in which a liquid gasket is applied to a sealing spot, the replacement recommending device comprising
a processing circuit configured to perform
an acquisition process of acquiring temperature information regarding the lubricant in the internal combustion engine, and
an output process of outputting a signal indicating that replacement of the lubricant is recommended by operating an output device when a parameter is equal to or greater than a predetermined value based on the temperature information acquired in the acquisition process, the parameter having a value that increases with an increase in a cumulative time in which a temperature of the lubricant is equal to or higher than a prescribed temperature, and the cumulative time being a cumulative time based on a time point at which the liquid gasket is applied to the sealing spot.

2. The replacement recommending device according to claim 1, wherein:
the output process includes a calculation process of dividing a temperature area that is equal to or higher than a predetermined temperature into a plurality of temperature subareas and calculating, as the parameter, a sum of values each of which is obtained by multiplying a cumulative time in which the temperature of the lubricant acquired in the acquisition process is in a corresponding one of the temperature subareas, by a weighting factor, and a determination process of determining whether the sum is equal to or greater than the predetermined value, the weighting factors for the temperature subareas being set such that a weighting factor for a higher temperature subarea among the weighting factors is greater than a weighting factor for a lower temperature subarea among the weighting factors, temperatures of the higher temperature subarea being higher than temperatures of the lower temperature subarea;
the output process is a process of outputting the signal indicating that the replacement of the lubricant is recommended when the sum is determined to be equal to or greater than the predetermined value; and the predetermined temperature is lower than the prescribed temperature.

3. The replacement recommending device according to claim 2, wherein:

the replacement recommending device is located outside a vehicle in which the internal combustion engine is mounted and includes a storage device and a communication device;

the acquisition process includes a process of storing, in the storage device, the temperature information regarding the lubricant acquired by communication using the communication device;

the calculation process is a process of calculating the sum based on time-series data regarding the temperature of the lubricant stored in the storage device; and the output process is a process of outputting the signal indicating that the replacement of the lubricant is recommended to a dealer of the vehicle by operating the communication device serving as the output device.

4. The replacement recommending device according to claim 3, wherein:

the acquisition process includes a process of acquiring information indicating that the lubricant has been replaced; and the processing circuit is configured not to perform the output process when there is information indicating that the lubricant has been replaced after the time point at which the liquid gasket is applied to the sealing spot.

5. The replacement recommending device according to claim 1, wherein:

the replacement recommending device is mounted in a vehicle in which the internal combustion engine is mounted; and the output process is a process of outputting the signal indicating that the replacement of the lubricant is recommended by operating an alarm serving as the output device.

6. A replacement recommending method of recommending replacement of a lubricant in an internal combustion engine in which a liquid gasket is applied to a sealing spot, the replacement recommending method comprising causing one or more computers to perform an acquisition process of acquiring temperature information regarding the lubricant in the internal combustion engine, and an output process of outputting a signal indicating that the replacement of the lubricant is recommended by operating an output device when a parameter is equal to or greater than a predetermined value based on the temperature information acquired in the acquisition process, the parameter having a value that increases with an increase in a cumulative time in which a temperature of the lubricant is equal to or higher than a prescribed temperature, and the cumulative time being a cumulative time based on a time point at which the liquid gasket is applied to the sealing spot.

7. The replacement recommending method according to claim 6, wherein the output process includes a calculation process of dividing a temperature area that is equal to or higher than a predetermined temperature into a plurality of temperature subareas and calculating, as the parameter, a sum of values each of which is obtained by multiplying a cumulative time in which the temperature of the lubricant acquired in the acquisition process is in a corresponding one of the temperature subareas, by a weighting factor, and a determination process of determining whether the sum is equal to or greater than the predetermined value, the weighting factors for the temperature subareas being set such that a weighting factor for a higher temperature subarea among the weighting factors is greater than a weighting factor for a lower temperature subarea among the weighting factors, temperatures of the higher temperature subarea being higher than temperatures of the lower temperature subarea;

the output process is a process of outputting the signal indicating that the replacement of the lubricant is recommended when the sum is determined to be equal to or greater than the predetermined value; and the predetermined temperature is lower than the prescribed temperature.

8. A non-transitory storage medium storing a replacement recommending program that is a program for recommending replacement of a lubricant in an internal combustion engine in which a liquid gasket is applied to a sealing spot, the replacement recommending program being executable by one or more computers, and causing the one or more computers to perform processes comprising:

an acquisition process of acquiring temperature information regarding the lubricant in the internal combustion engine; and an output process of outputting a signal indicating that the replacement of the lubricant is recommended by operating an output device when a parameter is equal to or greater than a predetermined value based on the temperature information acquired in the acquisition process, the parameter having a value that increases with an increase in a cumulative time in which a temperature of the lubricant is equal to or higher than a prescribed temperature, and the cumulative time being a cumulative time based on a time point at which the liquid gasket is applied to the sealing spot.

9. The non-transitory storage medium storing the replacement recommending program according to claim 8, wherein the output process includes a calculation process of dividing a temperature area that is equal to or higher than a predetermined temperature into a plurality of temperature subareas and calculating, as the parameter, a sum of values each of which is obtained by multiplying a cumulative time in which the temperature of the lubricant acquired in the acquisition process is in a corresponding one of the temperature subareas, by a weighting factor, and a determination process of determining whether the sum is equal to or greater than the predetermined value, the weighting factors for the temperature subareas being set such that a weighting factor for a higher temperature subarea among the weighting factors is greater than a weighting factor for a lower temperature subarea among the weighting factors, temperatures of the higher temperature subarea being higher than temperatures of the lower temperature subarea;

the output process is a process of outputting the signal indicating that the replacement of the lubricant is recommended when the sum is determined to be equal to or greater than the predetermined value; and the predetermined temperature is lower than the prescribed temperature.

* * * * *